(12) United States Patent  
Bustamante Grant et al.

(10) Patent No.: US 8,350,241 B2  
(45) Date of Patent: Jan. 8, 2013

(54) RADIOLOGICAL PROTECTION DEVICE

(75) Inventors: Jorge Bustamante Grant, Santiago (CL); Max Johansson Fuenzalida, Santiago (CL); Miguel San Martin Cancino, Santiago (CL)

(73) Assignee: Surikat S.A., Santiago (CL)

( * ) Notice: Subject to any disclaimer, the term of this patent is extended or adjusted under 35 U.S.C. 154(b) by 186 days.

(21) Appl. No.: 12/734,011

(22) PCT Filed: Oct. 2, 2008

(86) PCT No.: PCT/EP2008/063251  
§ 371 (c)(1),  
(2), (4) Date: Aug. 12, 2010

(87) PCT Pub. No.: WO2009/043912  
PCT Pub. Date: Apr. 9, 2009

(65) Prior Publication Data  
US 2010/0308238 A1    Dec. 9, 2010

(30) Foreign Application Priority Data  
Oct. 2, 2007   (CL) .................................. 2846-2007

(51) Int. Cl.  
*G21F 3/00* (2006.01)

(52) U.S. Cl. ................. 250/515.1; 250/516.1; 250/519.1

(58) Field of Classification Search ................. 250/515.1  
See application file for complete search history.

(56) References Cited

U.S. PATENT DOCUMENTS

| | | | |
|---|---|---|---|
| 4,859,853 A * | 8/1989 | Kronenberg | 250/370.07 |
| 5,045,708 A | 9/1991 | Cooper | |
| 5,247,182 A | 9/1993 | Servant | |
| 6,595,637 B2 * | 7/2003 | Ahsbahs et al. | 351/159.42 |
| 6,674,087 B2 * | 1/2004 | Cadwalader et al. | 250/515.1 |
| 8,185,360 B2 * | 5/2012 | Eakins et al. | 703/1 |
| 2007/0255248 A1 * | 11/2007 | Hendren et al. | 604/395 |

FOREIGN PATENT DOCUMENTS

DE    297 12 294    10/1997

* cited by examiner

*Primary Examiner* — Phillip A Johnston  
(74) *Attorney, Agent, or Firm* — John H. Dodds

(57) ABSTRACT

A radiation protection device, wherein it includes functional areas where anthropometric and adhesive material are located in the same or other discreet area. It also includes a use recording and/or control system.

9 Claims, 19 Drawing Sheets

FIGURE 3a

| Penis dimension study according to age | | |
|---|---|---|
| | Penis size | |
| Age (months) | Length (mm) | Diameter (mm) |
| 1.0 | 33.1 | 12.20 |
| 5.0 | 35.2 | 13.20 |
| 11.0 | 36.5 | 13.30 |
| 24.0 | 37.7 | 13.50 |
| 36.0 | 39.7 | 14.30 |
| 48.0 | 44.1 | 15.20 |
| 60.0 | 45.2 | 14.50 |
| 72.0 | 45.5 | 15.20 |
| 82.2 | 45.7 | 15.00 |
| 94.8 | 46.0 | 15.60 |
| 106.8 | 47.2 | 16.30 |
| 118.8 | 47.7 | 16.20 |
| 130.8 | 48.0 | 17.00 |
| 142.8 | 49.3 | 17.70 |
| 154.8 | 58.4 | 20.70 |
| 166.8 | 69.2 | 23.80 |
| 178.8 | 90.5 | 28.00 |

FIGURE 3b

| Prosthesis adult testicle size (Promedón) | | |
|---|---|---|
| Size | Height mm | Thick mm |
| T-Small | 31 | 23 |
| T-Medium | 37 | 28 |
| T-Large | 42 | 32 |
| T-X Large | 47 | 34 |

| Testicle size according to Prader orchidometer ||||
| Age | Height mm | Width mm | Volume ml |
|---|---|---|---|
| Childhood | 14.2 | 8.4 | 1 |
| Childhood | 17.9 | 10.6 | 2 |
| Childhood | 21.9 | 13.2 | 3 |
| Early puberty | 24 | 14.4 | 4 |
| Early puberty | 25.7 | 15.7 | 6 |
| Interm. puberty | 29.7 | 17.99 | 8 |
| Interm. puberty | 33.1 | 20.2 | 10 |
| Late puberty | 36.2 | 21.9 | 14 |
| Late puberty | 37.1 | 22.4 | 16 |
| Adult | 38.2 | 23 | 18 |
| Adult | 44.6 | 26.3 | 25 |

| Representative sizes and testicle range according to dimensions in figures 4a and 3b | | | | | | Penis size | |
|---|---|---|---|---|---|---|---|
| Age | Age range | width mm | Width range | Height mm | Height range | Volume ml | Diameter mm | Diam. range |
| 0 - 9 | Childhood | 13,2 | (12 - 16) | 21,9 | (20 - 27) | 3 | 16,3 | (15 - 18) |
| 10 -12 | Early puberty | 17,99 | (15 - 20) | 29,7 | (26 - 34) | 8 | 20 | (17 - 26) |
| 13 - 15 | Late puberty | 22,4 | (19 - 28) | 37,1 | (33 - 43) | 16 | 28 | (25 - 35) |
| 16 - XX | Adult | 34 | (26 - 35) | 47 | (42 - 48) | 30 | 40 | (34 - 41) |

| Testicle protection sizes according to max. ranges, Table 5a. | | | | Space of the peni |
|---|---|---|---|---|
| Years | Age range | Width mm | Height mm | Diameter n |
| 0 - 9 | Childhood | 32.4 | 48.7 | 20 |
| 10 -12 | Early pub. | 42 | 59.9 | 24.8 |
| 13 - 15 | Late pub. | 59 | 83.4 | 34 |
| 16 - XX | Adult | 86 | 115 | 48 |

| A | 3 month – 2 year |
|---|---|
| B | 3-5 year |
| C | 7-9 year |
| D | 10-13 year |
| E | >13 year |

| Formats | Dimensions of girls' pelvis in millimeters (mm) | | | | | | |
|---|---|---|---|---|---|---|---|
| Age-months | Height (mm) | High range | Width (mm) | Width range | Symphysis Di | Symph. range | Size (cm) |
| 0 - 3 | 28 | (20 - 32) | 40 | (36 - 44) | 3,6 | (3,5 - 3,7) | 53 - 60 |
| 3 - 12 | 34 | (28 - 38) | 48 | (42 - 54) | 3,8 | (3,6 - 4) | 61 - 70 |
| 12 - 24 | 38 | (34 - 48) | 56 | (52 - 64) | 4,2 | (3,9 - 4,6) | 71 - 86 |
| 24 - 60 | 52 | (44 - 68) | 68 | (62 - 86) | 5 | (4,5 - 5,7) | 87 - 108 |
| 60 - 108 | 72 | (66 - 78) | 90 | (84 - 98) | 6,4 | (5,6 - 7) | 109 - 133 |
| 108 - 144 | 92 | (76 - 102) | 115 | (96 - 120) | 7,8 | (6,9 - 8,6) | 134 - 151 |
| 144 - 180 | 108 | (100 - 112) | 134 | (118 - 142) | 9 | (8,5 - 9,6) | 152 - 162 |
| 180 - 252 | 126 | (110 - 130) | 156 | (140 - 160) | 10,5 | (9,5 - 10,6) | 163 - 165 |

Hip exam on female child 2 months and 15 days of age.
Manually cut out lead piece by a technician used for protection
purposes.

Radiography with a shield by Kirks from 2 months to 3 years of age.

3 sizes:

1 - Small (4" x 4½")
2 - Medium (6" x 7")
3 - Large (7-½" x 9")

PNWX Gonad Shields by *Oprax Medical International.*

3 Sizes

1 - 3" x 5"
2 - 5" x 7"
3 - 7" x 9"

FIGURE 22: *Percentile 50*
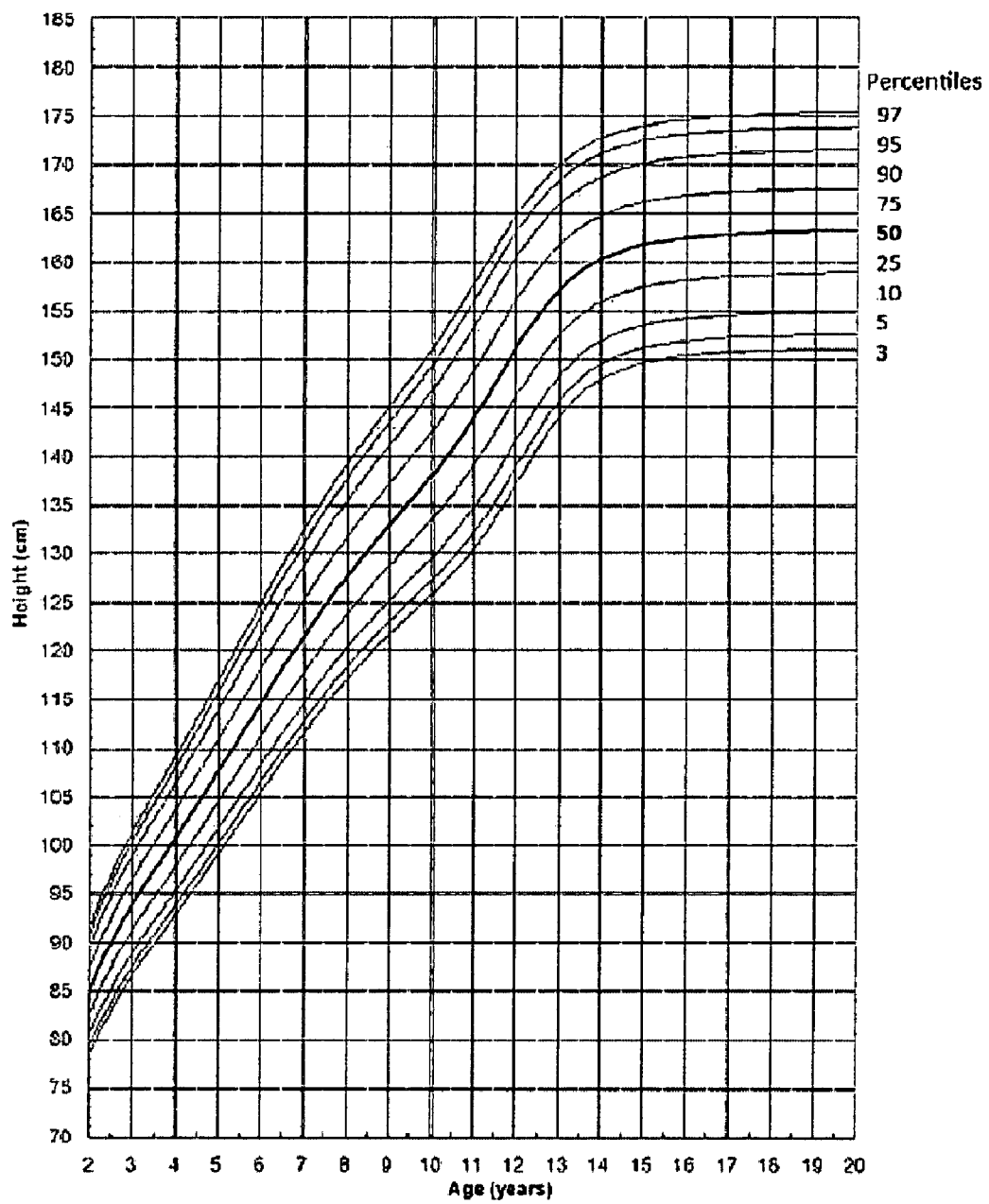
Height by age, percentiles 2-20 year old girls
Design by Ernest M. Post, MD. Completed by Luis Romero.

FIGURE 23: *Percentile 50*
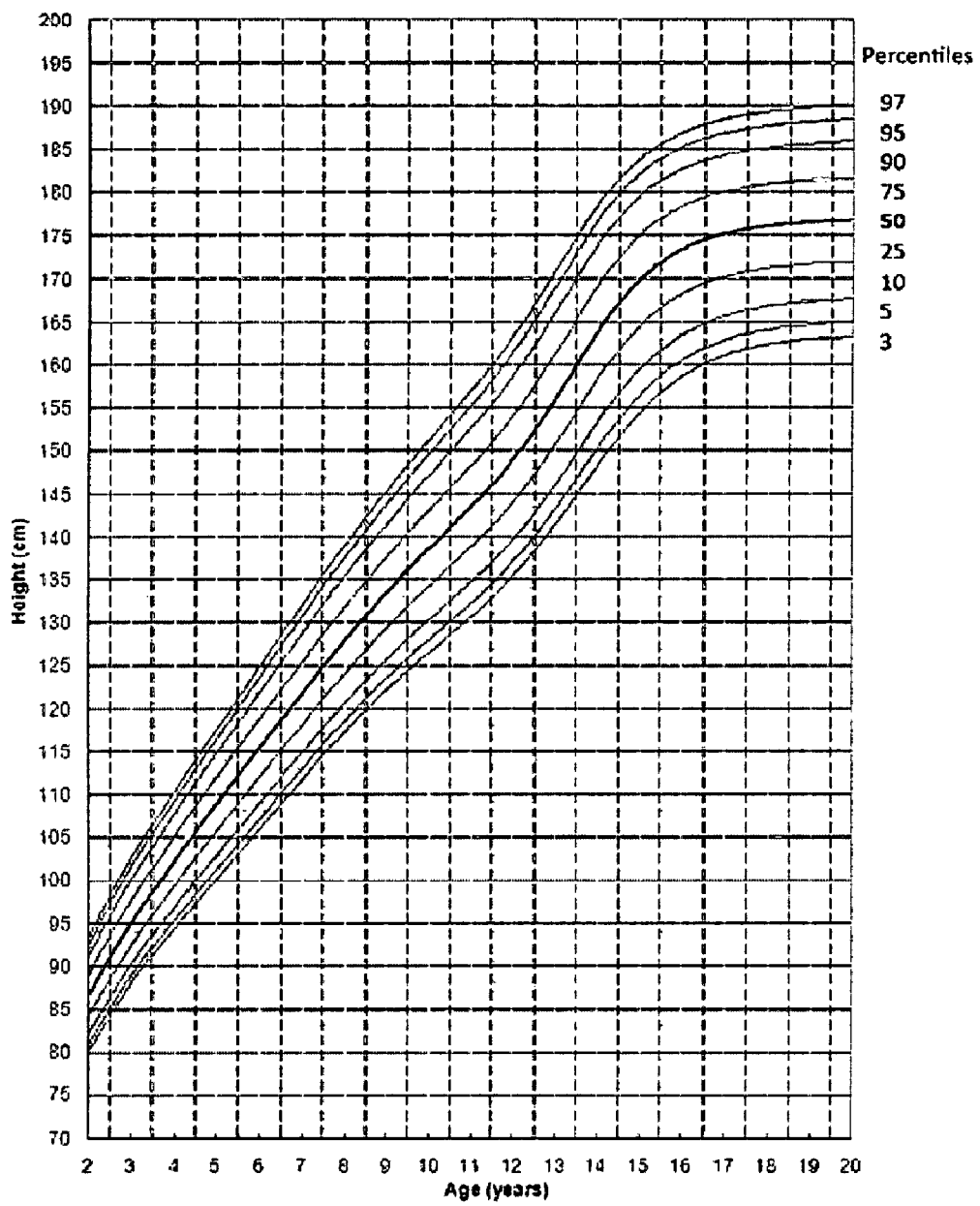
Height by age Percentiles 2-20 year old boys
Designed by Ernest M. Post, MD. Completed by Luis F. Romero

RADIOLOGICAL PROTECTION DEVICE

This invention corresponds to a radiological protection device for patients' middle area, particularly to protect the area between hips and pelvis in order to safeguard the user's genital and gonad area from radiation.

BACKGROUND

In nature, as well as in the environment created by man, we are permanently exposed to radiations such as solar, electromagnetic, and nuclear, many of which are, in different intensity, harmful to life and organism survival. However, technological advancement has allowed using the said radiations, but without eliminating their harmful components. As a result, the human body has been progressively exposed to all types of radiations, and parallel efforts have been made to improve radiation protection procedures and devices. (www.cancer.gov/cancertopics/causes/radiation-risks-pediatric-CT; www.niehs.nih.gov/oc/news/canceragents.htm; COUNCIL DIRECTIVE 97/43/EURATOM, Jun. 30, 1997).

Anatomic structures such as part of the chest, thyroids, genitals, and gonads, are highly sensitive and deeply harmed by exposure to different types of radiation. For this reason, efforts have been made to develop protection mechanisms in front of this type of radiations. Traditionally, high molecular weight metals have been applied, such as lead, as radiological protection. Lead, being an element that adds a large weight to devices to which it is incorporated, becomes of difficult application, presents certain toxic characteristics, and certain ranges of natural radioactivity. For this reason, new technologies have been developed as protection against radiation. These are products of high plasticity in their applications and easy to work with, environment friendly, and less toxic for users and operators.

Technologic solutions have been proposed, such as those described in U.S. Pat. No. 5,778,888, which proposes special radiation protection devices for men and women. However, compared to this invention, there is an outstanding difference in assigning a correct protection to properly protect the gonad region in each case. Also, fastening systems are complex and uncomfortable for the user and do not guarantee that the original position will be maintained.

On the other hand, there are proposals as the one described in U.S. Pat. No. 5,247,182, where an essentially rectangular gonad protection device is dealt with. Compared to this invention, these proposals make patients' X-ray evaluation difficult because the surface covered by these devices is larger than necessary, and it may hide areas that require be seeing and diagnosing. This way, it is possible that repeated exposures and repeated evaluations are required in order to obtain an image that meets the medical evaluation requirements. On the other hand, this invention is accurately placed on the area to be protected, minimizes the need for repeated exposures because it involves a minimum intervention of the areas that may require exposure and evaluation and, therefore, the amount of radiation on the patient decreases.

The said complications also appear in the proposal published in U.S. Pat. No. 5,523,581, where the thyroids protection device may cover a surface larger than necessary for an effective protection. This, together with the system fastening characteristics, multiplies the risk of an incorrect use; therefore, they increase the patients' risks and the possibility to repeat the evaluation.

Alternative solutions have been proposed in U.S. designs D 457,690 and D 457,689 where, in the case of men and women, respectively, gonad radiation protection devices of daily use have been published. Although the said proposal means an important contribution with regards to ease of use and devices' portability, it does not guarantee a correct positioning for a correct radiation protection, and does not guarantee their safe position which, in the case of this invention, is directly addressed and guaranteed.

Commercially, different devices are available, as those offered by Oprax Medical, MedTec, RadPad, Shielding International, QuickMedical, or Pulse Medical, although none of them has shown the technical benefits and contribution proposed by this technique. In fact, FIGS. 19-20 show that use of these devices affect the correct visualization of structures relevant for radiological diagnosis.

In pediatrics radiology literature, different important references may be found, such as the book "PRACTICAL PEDIATRIC IMAGING: DIAGNOSTIC RADIOLOGY OF INFANTS AND CHILDREN", by DONALD KIRKS (ISBN: 0316494739), where contact gonad protection templates are described according to the patients' age (FIG. 10). As usual in medical literature, shields are described with a triangular and pointed geometric shape that increases size towards the lower end, as the arrow indicates. This means that the shield lacks an optimal shape to protect the pelvic cavity and, by being larger towards the cavity lower part, bone structures that are relevant for a medical diagnosis are covered, damaging the image quality which, in some cases, may imply repeating the examination (FIG. 18 *a-b*). This invention proposes a shape that has been adapted to the pelvic cavity, and its size increases the other way around, starting from its lower to its upper part, leaving the lower part free for medical diagnosis.

Currently, the shields' correct placement depends on the ability to locate the pelvic cavity through tact, as the area is invisible for the human eye. With this method, location is not accurate and many times the image quality is compromised, as important bone structures are covered for the diagnosis. This invention proposes the use an anthropometric point of reference, the pubic symphysis, which is joining through the "Anthropometric connecting point" present in the device in order to correctly place the radio/opaque material or the "radiation attenuation material" on the patient.

The present invention provides a system to protect patients from radiation providing protection to sensitive areas of the human body that are not of diagnostic interest. An example of this is to protect the reproductive glands or gonads, ovaries in girls and testes in boys, in the case of the ovaries, to take a frontal radiograph of the pelvis, the ovaries become lodged in the pelvic cavity, so you may provide protection to the pelvic cavity without obstructing bony parts of diagnostic interest, would give greater security and benefit to the patient, reducing the radiation dose in sensitive areas of the body.

Therefore, the technical solution this invention development provides aims at providing a device that offers a set of advantages and benefits with regards to technical alternatives. It is of advantage due to the flexibility and plasticity in its applications. Also, it provides a relatively high degree of comfort to the user, as well as the possibility to attenuate radiation for radiology personnel or people working with radioactive materials.

In addition, the invention offers a radiological protection system that allows incorporating beneficial qualities when operating it, such as a radiation attenuating system that may be sterilized and discarded, and complemented with other protection devices. However, the most significant contribution is accuracy and efficiency in radiological protection as a result of a precise, safe, and permanent positioning, according to the patient and/or user accurate anatomic parameter combination and adhesion and/or fastening systems.

DESCRIPTION OF FIGURES

This description, associated to the images, corresponds to the illustration of some embodiments preferred in this invention. In no way whatsoever it corresponds to, or seeks a restriction of the invention description or scope, nor does it correspond to exclusive representations for this invention.

FIG. 3a is a table that describes penis dimensions according to age, up to 14.9 year. This table mainly contains penis diameter data used as direct reference for the radiologicalal shield for males ("Penis Length and Diameter in Boys from 0 to 14", Dr. R. Anigstein. *Archivos Argentinos de Pediatría*, vol. 103 No 5, Buenos Aires, September/October 2005 (Print ISSN 0325-0075). Variables studied for this work were evaluation of pubertal development through the Tanner methods, testicle size with Prader orchidometer, as well as penis length and diameter while in repose. www.scielo.org.ar/scielo.php?script=sci_arttext&pid=S0325-00752005000500005&Ing=en&nrm=iso)

FIG. 3b is a table describing testicle prosthesis sizes for adults available in the market from companies such as Promedón. This table provides data on the minimum protection surface for the male radiologicalal shield. (www.promedon.cl)

FIG. 10 b is a table showing women's pelvis dimensions from infants to adults, and connects the said dimensions to the individuals' sizes and the distance from the anthropometric reference point corresponding to the pubic symphysis and the pelvic cavity start.

Figure 1:
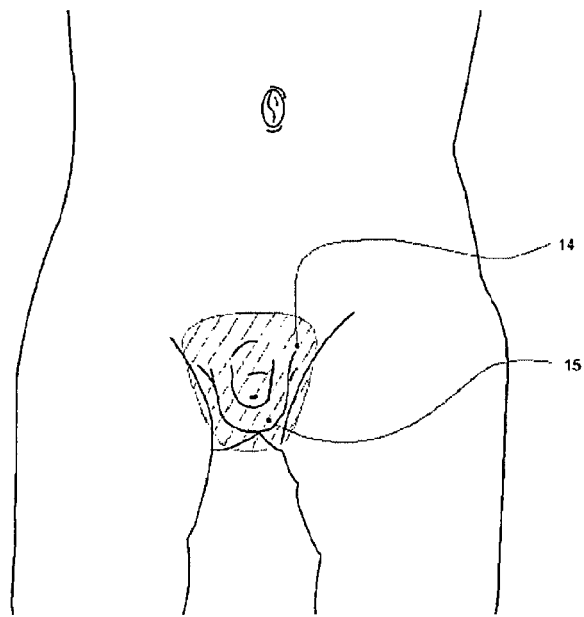
FIG. 1 shows a representation of the lower middle area of a boy, where (15) represents male gonads and (14) provides a scheme of the area to be protected. This representation may apply to all ages of a man.
Figure 2:
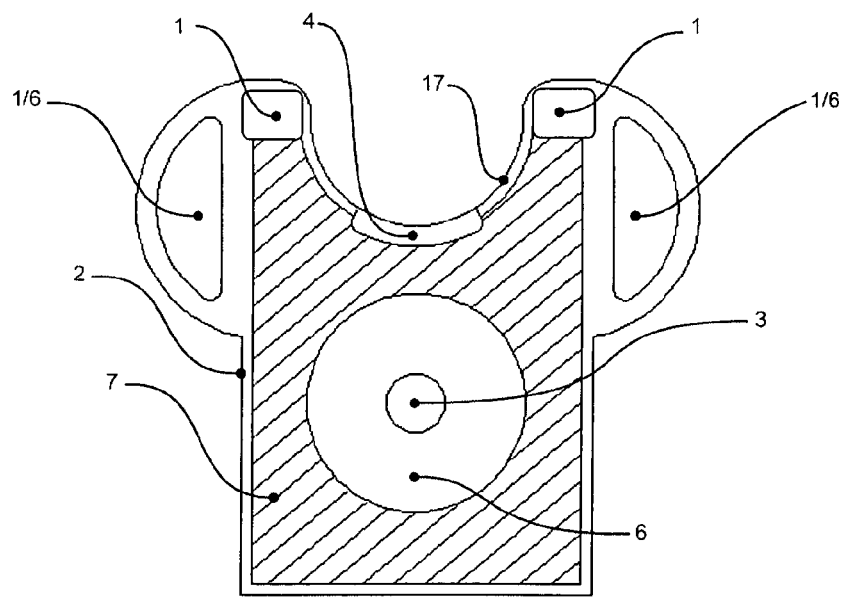
FIG. 2 shows a generic view of the proposed invention for males, which shows the device different areas and characteristics, independently from its geometric shape (1) represents a discreet functional area containing a fastening flange, (2) is an upper cover, (7) exposes the area that contains the radio-opaque material, (3) corresponds to a radiation indicator and its use, (4), corresponds to an "Anthropometric connecting point" related to the penis lower areas (6) corresponds to a discreet functional area containing a contact adhesive, and (17) corresponds to the diameter of the penis base area of location, according to the individual size variations as indicated in FIGS. 3a, 5a, 5b, and 6.
Figures 4A, 4B:
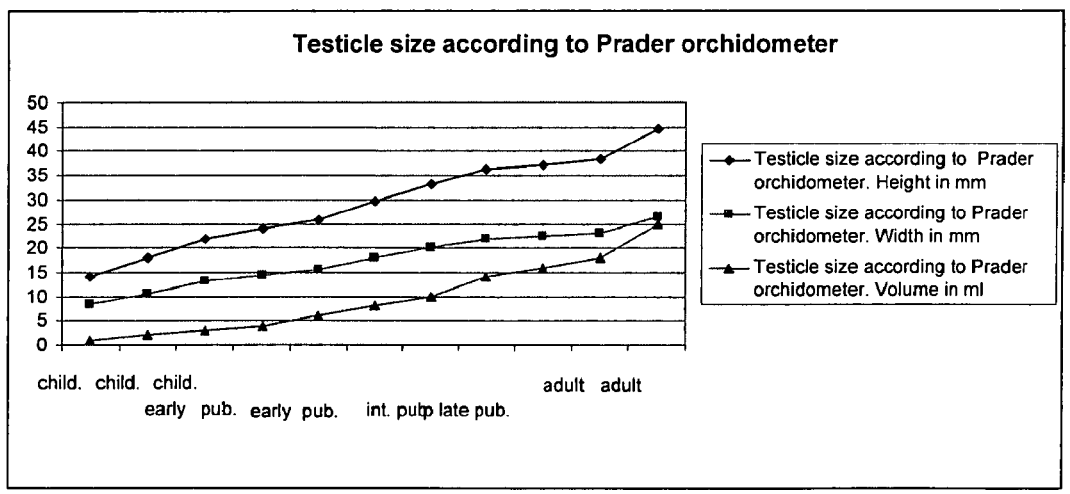
FIG. 4a is a table describing testicle sizes according to Prader orchidometer official sizes, and used to measure a patient's testicle size. This table provides data on testicle size according to age in different growth stages and complements table 3b. Reference: www.puberty101.com/p_orchidometer.shtml
FIG. 4b is a graphic representing table 4a, where an individual testicle growth curve is shown according to Prader orchidometer official sizes.
Figures 5A, 5B:
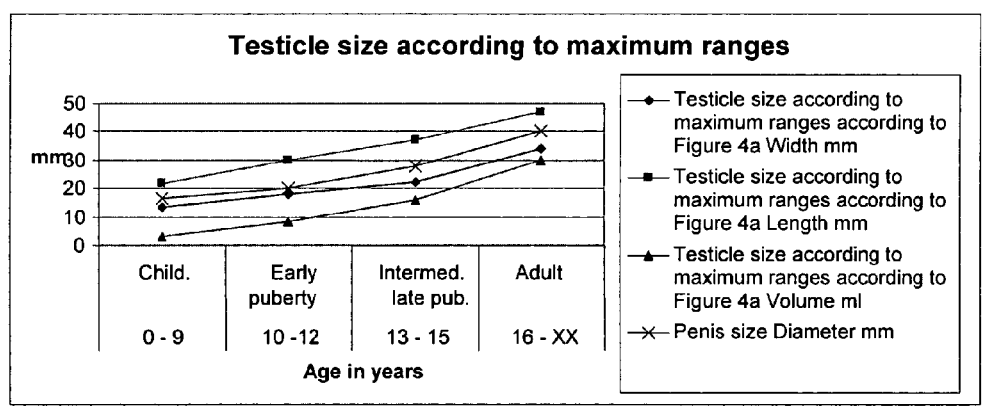
FIG. 5a is a table describing four testicle sizes and their maximum values according to age and the corresponding testicle dimension. This table shows the maximum values to be considered for male gonads in table 4a, and it is related to the penis base diameter according to age, as the anthropometric reference point on the penis root base which in joining to the "Anthropometric connecting point" present in the invention device, as shown in FIG. 1. (4) This shall allow a correct protection of the gonads base areas.
FIG. 5b is a graphic describing a testicle growth curve according to maximum ranges described in FIG. 5a. It is possible to see the relation existing between the said parameters' variation with age, which allows defining the correct protection value ranges.

and no movement during evaluation. Here, (18) is the radio-opaque shield according to the invention, and (12) is the area of interest for medical diagnosis which, in this particular case, is completely free for later diagnosis due to its correct format and location using the anthropometric reference point. and the "Anthropometric connecting point".

FIG. 22 is a chart showing size variations (height) in 2 to 20 year old females. Here, different percentiles are represented (exposed lines) and it is called Percentile 50. This information was used to link pelvic cavity size variation to size.

FIG. 23 is a chart showing size variation (height) in 2 to 20 year old females. Here, different percentiles are represented (exposed lines) and it is called Percentile 50. This information was used to link pelvic cavity size variation to size.

DESCRIPTION OF THE INVENTION

This invention is a radiological shield device that may be used on patients or operators during medical examinations, and/or it may also be used by/on individuals exposed to radiation environments, as in the case of health professionals working in radiology or operators or professionals handling radiation materials.

In particular, this invention includes a radiological shield device that effectively protects against radiations to which the user is exposed, thanks to guiding functional areas for the correct placement of the device. These guiding functional areas have a "Anthropometric connecting point" allowing positioning the radiological shield device on the human body so that it provides an effective radiation protection to the anatomic area that should be safeguarded during a probable or concrete radiological exposure, be it continuous, intermittent, or for short periods of time.

In one of its models, this protection shield has a radiological protection area with a given shape and size called, in whole, format that geometrically defines the device. Preferably, the invention device has different formats according to the patient's age and gender. This format purpose is to effectively cover the area to be protected, particularly genitals and/or gonads in humans, the pelvic cavity where ovaries are located in women, and testicles in men, without compromising or covering the neighboring or adjoining bone structure, fundamental parts that may be essential for a correct medical diagnosis.

In one model, this invention includes discreet functional areas that complement and facilitate the device correct placement and guarantee its effective protection during use. These areas have adhesive or fastening materials that allow maintaining the device on the anatomic position it was placed.

In an additional model, the radiological shield includes a device to record and control its use frequency and applications.

In another additional model, the device may contain additional radiological protection materials, substances, or means that may be permanent, interchangeable, or disposable. The said materials are usually known to an expert on the matter and may be found in organizations such as FDA, UNSCEAR, ICRP, ICNIRP, among other, which certify or approve their use. At the same time, compartments containing the said additional elements may be distributed in the entire device structure, be one or more than one, or even the device may be a compartment itself.

At the same time, the invention is related to the description of proportions, shapes, and sizes for a radiological protection area or item that may be incorporated to the said devices. The invention also refers to the use and application of the said radiological protection devices, area or item.

DETAILED DESCRIPTION OF THE INVENTION

This invention is related to a radiological protection device that effectively blocks radiation and is used on patient examinations and/or by persons who may be exposed to radiation environments, as in the case of health professionals working in radiology facilities or operators and professionals handling radiological materials.

In particular, this invention includes, in the one hand, a radiological protection shield for the trunks' lower part, corresponding to the pelvic area. In its upper part, this area contains part of intestines and other organs, while the pelvis contains genitals and gonads. Preferably, this invention includes a device designed to provide effective radiological protection to genitals, mainly gonads of the proposed device users. On the other hand, the device also could be used in the thorax area, where female breasts are located. Externally in this area, mammary glands are located, which are to be protected.

Figure 12:
FIG. 12 shows radiography with the pelvic cavity area that should be protected when X-rays are taken. Here (7) corresponds to the correct and recommended location for the radio-opaque material. In particular, it shows that the protection a device would provide according to the invention when the "Anthropometric connecting point" has been aligned with the patient's symphysis, which is the "Anthropometric reference point". In this case the patient is a woman.
Figure 21A:
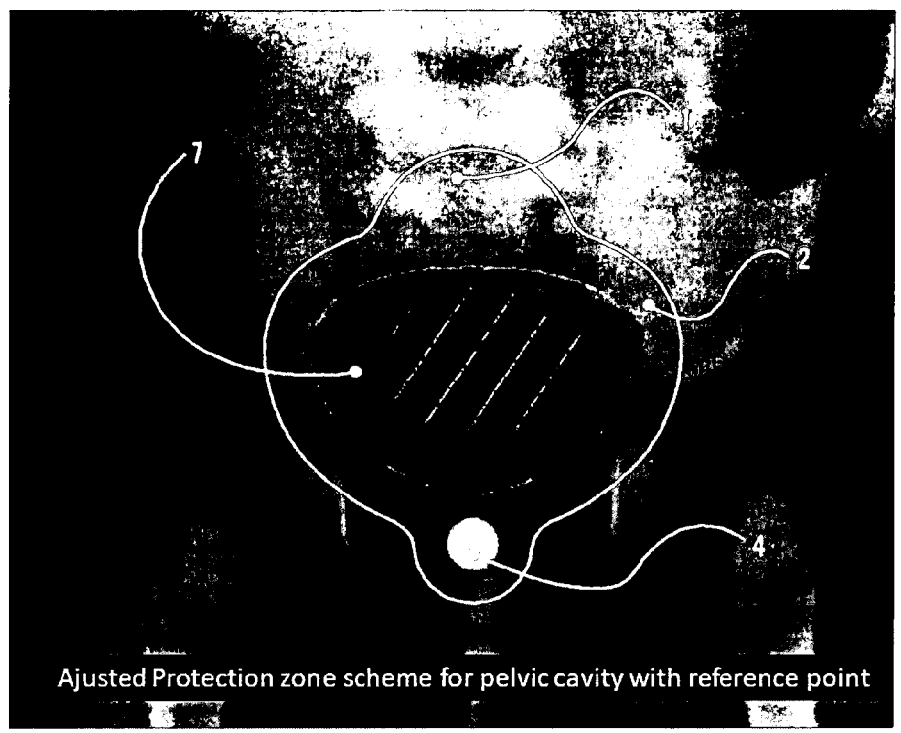
FIG. 21a corresponds to a radiography showing a scheme of protection area adjusted to pelvic cavity with point of reference according to invention device in a model proposed for females. Here, (1) is the fastening flange, (2) is the upper covering (front), (7) is the area where the radio-opaque material is located, and (4) corresponds to a "Anthropometyric connecting point"
Figure 21B:
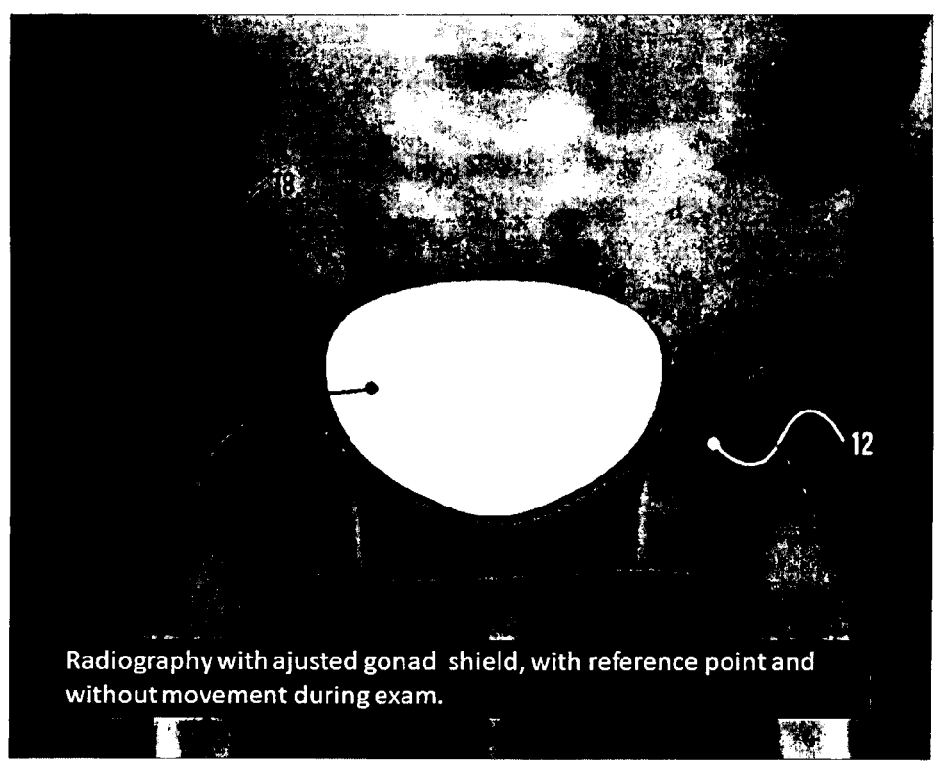
FIG. 21b corresponds to a radiography where an invention device model proposed for females has been used, it was adjusted to pelvic cavity with "Anthropometric connecting point".

The proposed devices' geometry (format) provides an effective radiological protection for gonads in the pelvic of any individual, female or male. This particular format is mainly defined by factors such as: gender of the user/patient, the individual's size, his age, and the dimension of the area where gonads are located. Studies carried out (see FIGS. 3a-6, 10b, and 11a-11c) define the radiation protection area format, which may be called radiological protection item, whose dimensions meet the age, size, and gender of the patient, as indicated above. The precise location of the said radiological protection area or item should be at a location established according to an anthropometric reference point in the invention devices in order to correctly place the shield or device on the patient, provide a correct protection during radiological examinations as shown in FIGS. 12 and 21b, and avoid multiple exposures due to the hiding of areas of diagnosis interest. This characteristic and function are complied with independently from this invention device format.

All formats, or sizes according to age, for the radiological protection area or item defined in this invention are related to the growth range in the gonad area which, in the case of women, is the pelvic cavity at different ages (see curve in FIGS. 11a-11c), shown according to a specific height and width (see FIG. 13), but in the case of men, it is the testicle growth at different ages (see curve in FIGS. 3a-6). With no intention to restrict the number of formats to be defined for the radiological protection areas or items shown in FIGS. 7 and 13, it is possible to consider seven radiological protection final formats for adult females and four formats for males between the ages of zero (0) months and twenty (20).

Figure 15A:
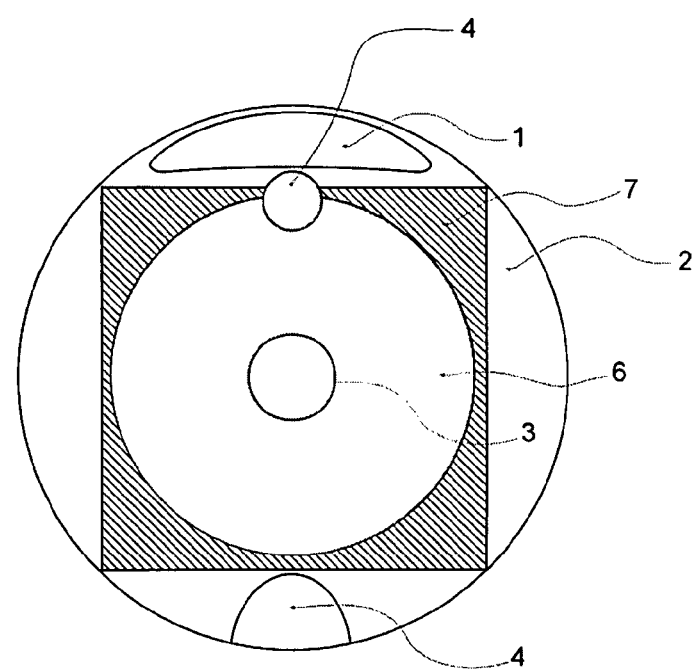
FIG. 15a shows a device general view, according to the invention, where the device different areas and characteristics may be seen, independently from the geometric shape and the patient's gender. Here, (1) represents a discreet functional area containing a fastening flange, (2) is an upper covering, (7) shows the area containing the radio-opaque material, (3) corresponds to a radiation indicator and its use, (4) corresponds to an anthropometric connecting point, and (6) corresponds to a discreet functional area containing a contact adhesive.
Figure 15B:
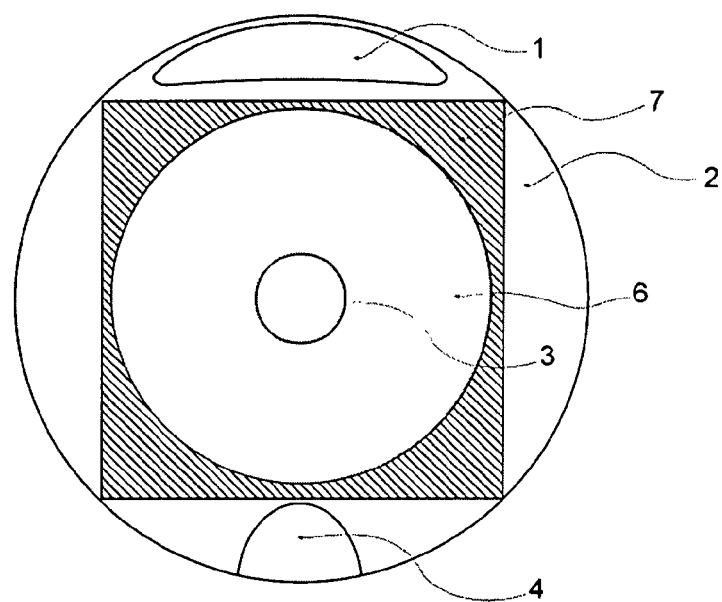
FIG. 15b shows a generic view of a device proposed for females according to the invention, where the device different areas and characteristics are shown, independently from their geometric shape and the patient's gender. Here, (1) represents a discreet functional area containing a fastening flange, (2) is an upper covering, (7) shows the area containing the radio-opaque material, (3) corresponds to a radiation indicator and its use, (4) corresponds to an anthropometric connecting point, and (6) corresponds to a discreet functional area containing a contact adhesive.
Figure 15C:
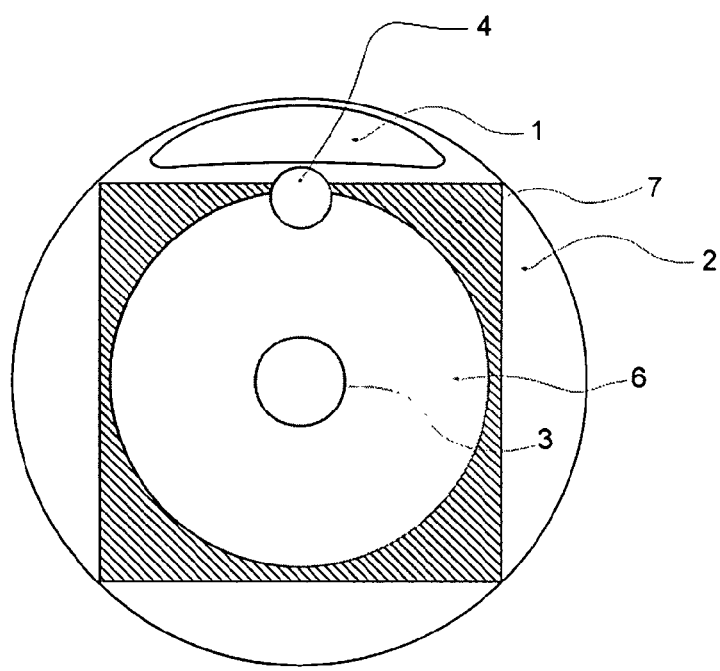
FIG. 15c shows a generic view of a device proposed for males according to the invention, where the device different areas and characteristics are shown, independently from their geometric shape and the patient's gender. Here, (1) represents a discreet functional area containing a fastening flange, (2) is an upper covering, (7) shows the area containing the radio-opaque material, (3) corresponds to a radiation indicator and its use, (4) corresponds to an anthropometric connecting point, and (6) corresponds to a discreet functional area containing a contact adhesive.

These invention devices include the said radiological protection zones or items, together with other components that define them and allow determining an invention modality, with no intention to restrict them, as shown in FIG. 15a. These components that may be incorporated to the invention devices are an anthropometric guiding area (4), and/or a fastening area (1), and/or an adhesion area (6) and/or an indication or radiation or use record area.

In an embodiment additional to the invention, use of a radiological protection device and/or area or item is proposed in order to provide an effective radiological protection, which may be in the pelvis and gonad area, as well as in the thorax area corresponding to female breasts or mammary glands. The invention means general geometry is appropriate for thorax application due to the said glands' external position and their size and shape, as they are able to contain breasts and cover their most important surface.

Therefore, the inventions' devices include discreet functional areas in the devices' structural components that define the location of these preferable components mentioned and detailed below. Preferably, in these functional areas only one of the said structural components could be available; however, in some embodiments at least two of the said components could be available in the same discreet area.

Under a favorite invention embodiment, the device includes a radio protection zone or item with a given format, as indicated in this document. Preferably, the device also includes anthropometric coordinates located in discreet functional areas that allow positioning the radiological protection device on the human body in such a way that the radiological protection area or item provides an effective protection during radiological exposure, be it a radiological examination or their use by health professionals and technicians exposed to radiation during work. In one favorite embodiment, the invention female gonad protection device, the anthropometric guiding point, allows positioning and aligning the device with the pubic symphysis or pubic bone through the bone direct contact with the device anthropometric point. This is a specific anthropometric coordinate that allows correctly placing the device for a correct gonad protection. In another favorite mode, the male gonad protection device, the anthropometric guiding point, allows positioning and aligning the device with a tangential point at the basis of the penis, establishing a link between the said point and the device anthropometric guiding point. This coordinate allows positioning the protection device in a way that the protection area or item covers the testicles which, in this case, and different from females, are externally located.

Therefore, this invention has a variety of radiological protection devices and area embodiments and formats, according to the user's age and his/her gender, and even according to their ethnical group. In fact, this invention would correspond, particularly, to a variety of devices whose dimensions and shapes are related to gonad location in male and female anatomy, and to their development at the moment the device is used. The purpose is to cover the object area, such as the female pelvic cavity, without covering the bone structure to be diagnosed.

Figures 6, 7:
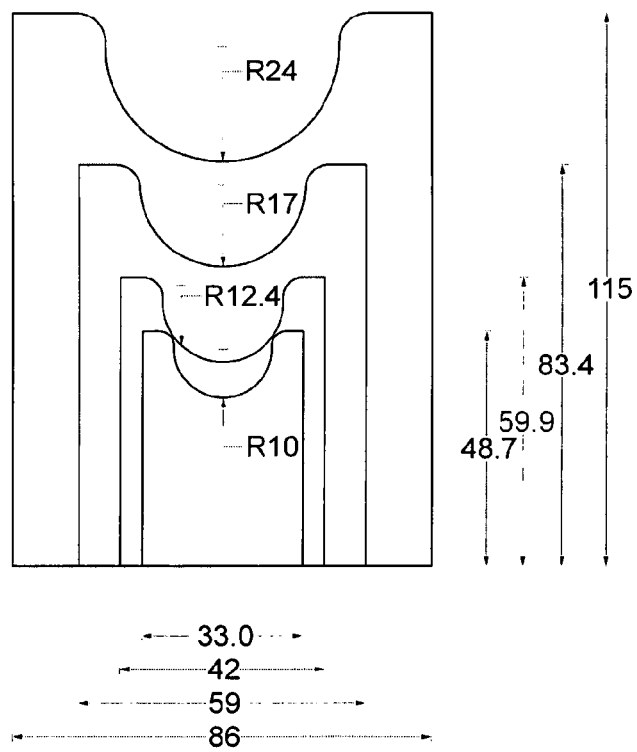
FIG. 6 is a table describing the final protection sizes expressed in four formats according to the man's age. These are based on the data shown in FIGS. 3a-5b, which links gonads' measures to the anthropometric information provided by the penis root basis, making it possible to define radiological shields' dimensions most appropriate for males.
FIG. 7 represents a progression and its corresponding dimensions for four radiological protection areas format (front view) for a man's pelvic and gonad area for his different adulthood stages. The said formats are incorporated in devices such as those described in FIG. 2.
Figure 8:
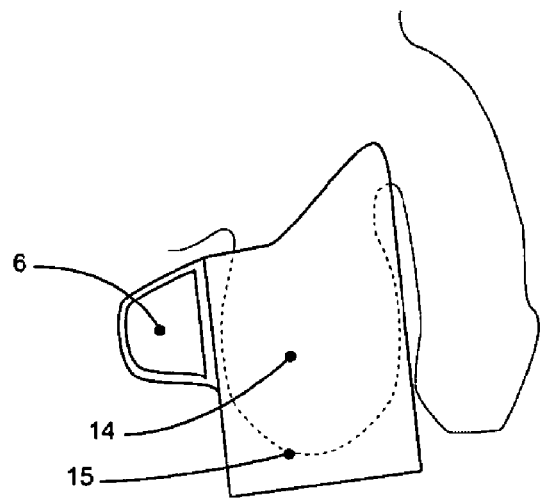
FIG. 8 corresponds to a side view of male gonads, where an invention device is located in a model proposed for males. Here, (6) is a contact adhesive area, (15) is a side view of male gonads, and (14) is the area to be protected. This invention method protects male gonads in an angle from 180° to 360° through their longitudinal axis, providing protection during front and side examinations.
Figure 9:
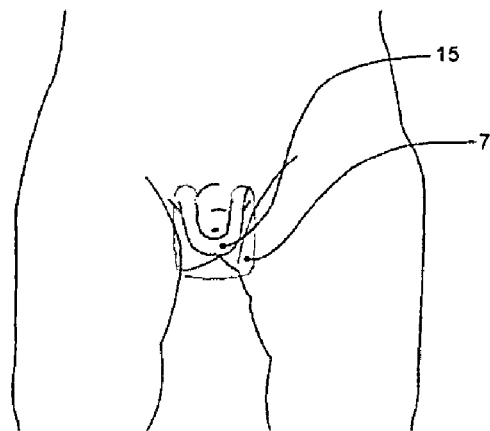
FIG. 9 corresponds to a front view of the radiological protection that FIG. 7 format would provide to male gonads, where the invention device is located in a way proposed for males, where (7) is the location of radio-opaque material, and (15) are male gonads.
Figures 10A, 10B:
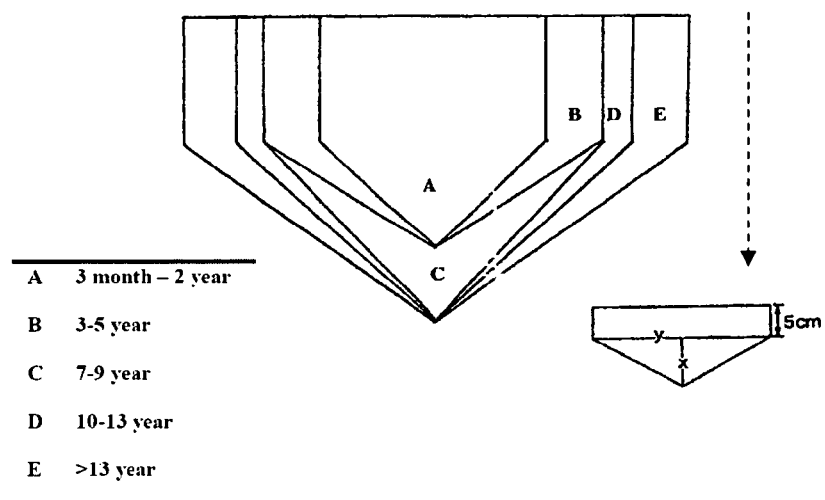
FIG. 10a corresponds to the scheme of the radiological shield proposed by Kirks. In this design, the protection area grows to the sides (y) and downwards (x), according to the coordinates indicated in the Figure reduction.
Figure 11A:
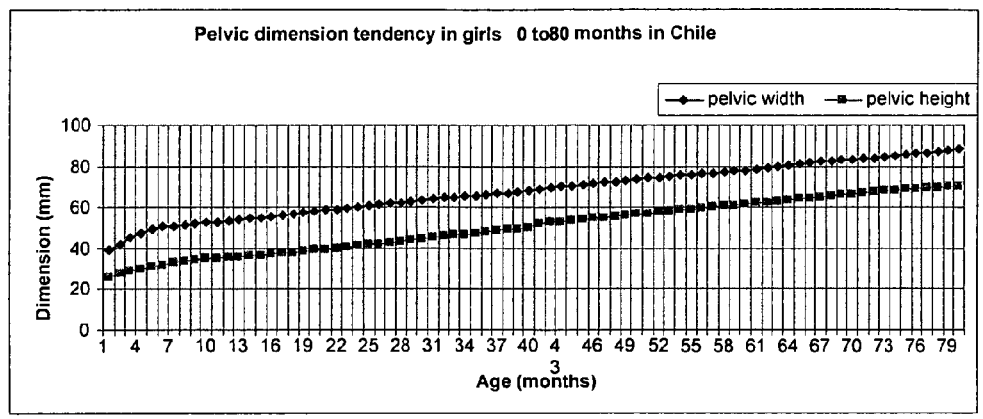
FIGS. 11a-11c correspond to charts showing the pelvic cavity growth dimensions (width and height) in females from 1 to 252 months. Each point in the chart is the result of at least one measurement.
Figure 11B:
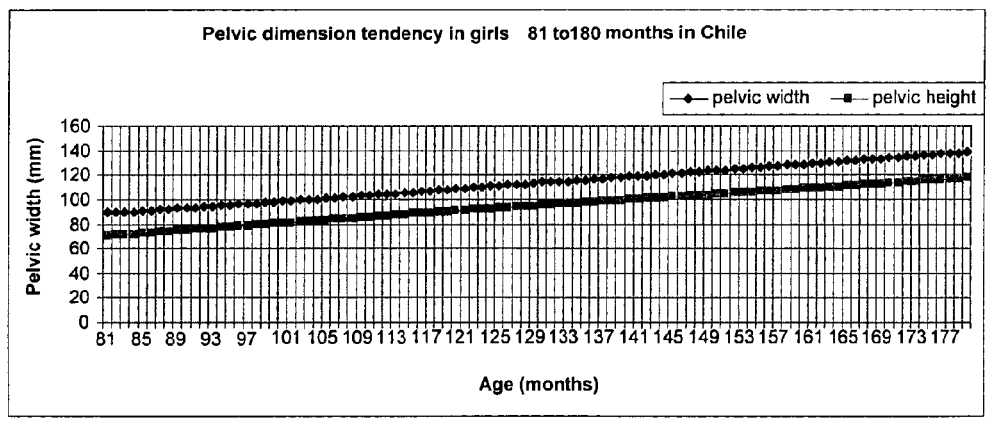
Figure 11C:
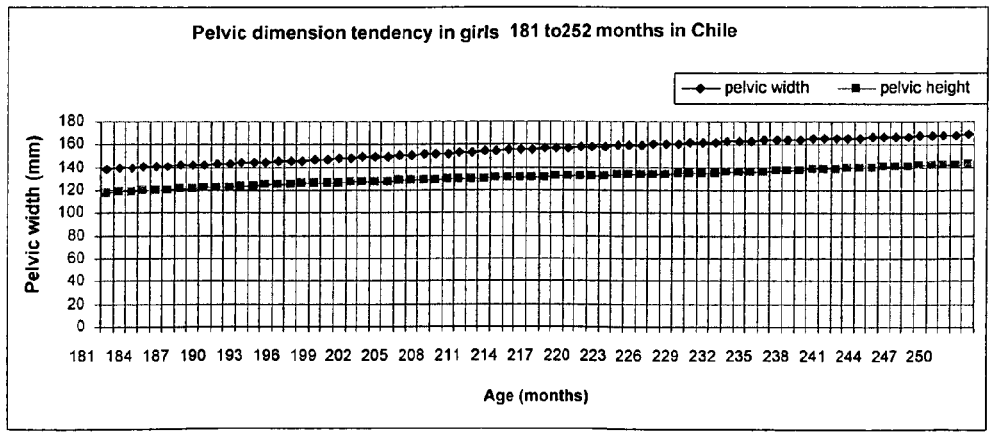
Figure 13:
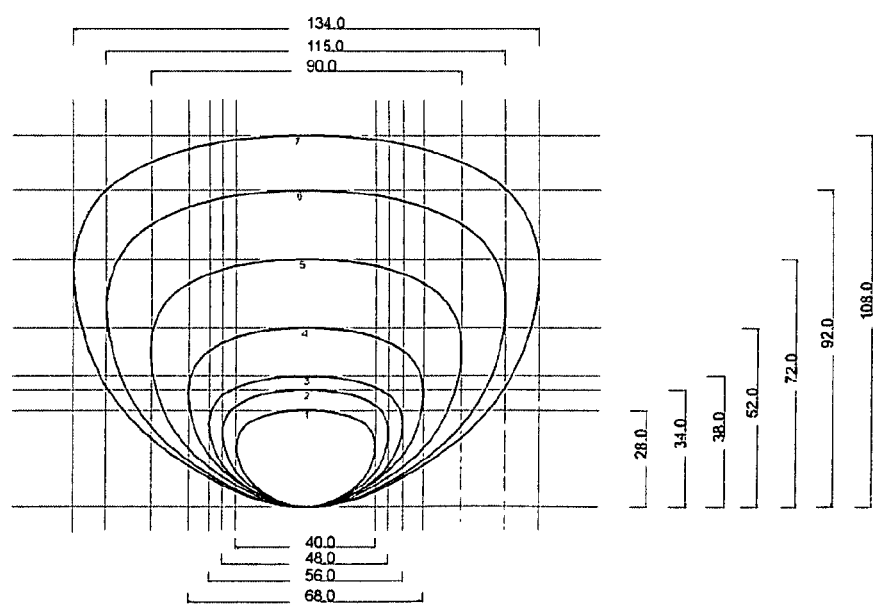
FIG. 13 shows a set of seven formats for the radiological protection area that these invention devices could include. The said formats correspond to heights and widths that represent a certain period of female growth, as indicated in the table in FIG. 10b. Each format selection criterion includes a growth period, as extensive as possible for each format without the risk of covering the bone structure when taking radiography.

According to the invention, means described herein, such as the radiological protection device and area, are provided in different sizes and different geometric shapes, where both parameters (shape and size) generate the favorite shield indicated for each age (FIGS. 7 and 13). Selection criteria for each format aims at including a growth period, as extensive as possible, for each format without covering the adjoining bone structure of diagnosis interest at the moment X-rays are taken. These formats are based on a study of pelvic examinations in patients up to 180 months (15 year olds), complemented by height percentiles according to age in boys and girls, separately, (FIGS. 21a and 21b), until twenty (20) year olds. Height percentile provides the average information on skeleton growth and its normal ranges according to age. When comparing the pelvic cavity specific growth with the rest of the skeleton, it is possible to determine a pelvic cavity growth curve from age 15 to 20 (www.cdc.gov/growthcharts/). The study, through growth curves and extrapolations (FIGS. 11a-11c), shows pelvic cavity development at different ages and physiologic development stages. This curve allows establishing an undefined number of sizes, according to ages included in each one of them.

The inventions' radiological protection devices and areas are proportional to diameter or height and width. According to evidence provided in the Figures, it is possible to notice that the said proportionality, in the case of radiological protection areas, is different according to the individual's gender. For females, the said height-width proportion is preferably around 0.4 to 1.2, more preferably around 0.6 to 0.9, and most preferably around 0.65 to 0.85. In the case of males, the said width-length proportion is around 0.4 to 1.0, more preferably between 0.5 and 0.8, and most preferably around 0.60 to 0.75. However, favorite format for male and female genders are indicated in FIGS. 7 and 13, respectively. Table 1 contains examples of favorite formats through seven different sizes for women that define the radiation protection functional area of the device containing the radio-opaque material which, therefore, conditions its size and shape.

TABLE 3

| | Age in months | Height (mm) | Width (mm) |
|---|---|---|---|
| 1 | 0-3 | 28 | 40 |
| 2 | 3-12 | 34 | 48 |
| 3 | 12-24 | 38 | 56 |
| 4 | 24-60 (2-5 year) | 52 | 68 |
| 5 | 60-108 (5-9 year) | 72 | 90 |
| 6 | 108-144 (9-12 year) | 92 | 115 |
| 7 | 144-180 (12-15 year) | 108 | 134 |

Therefore, each format considers a given age of the patient with the purpose of simplifying production and use of the device. Also, the growth curve shows that hip anthropometric differences among different ages vary very little (FIGS. 11a-11c), for which reason it was decided that it is not necessary to use different formats for each month or year's growth. The seven formats determine and condition the size of the specific functional area that contains the radio-opaque material (FIG. 13).

In an embodiment for men, it was concluded that there is a possibility to establish formats that cover certain age ranges (FIG. 6).

According to this invention, protection areas could be used independently from the patient's gender and from the device. However, formats up to 12 month old are safer to independently use on boys or girls in order to cover testicles and the pelvic cavity to protect them from radiation, which could be achieved by simply rotating the device. This is due to the similar gonad size for both genders.

Figure 14:
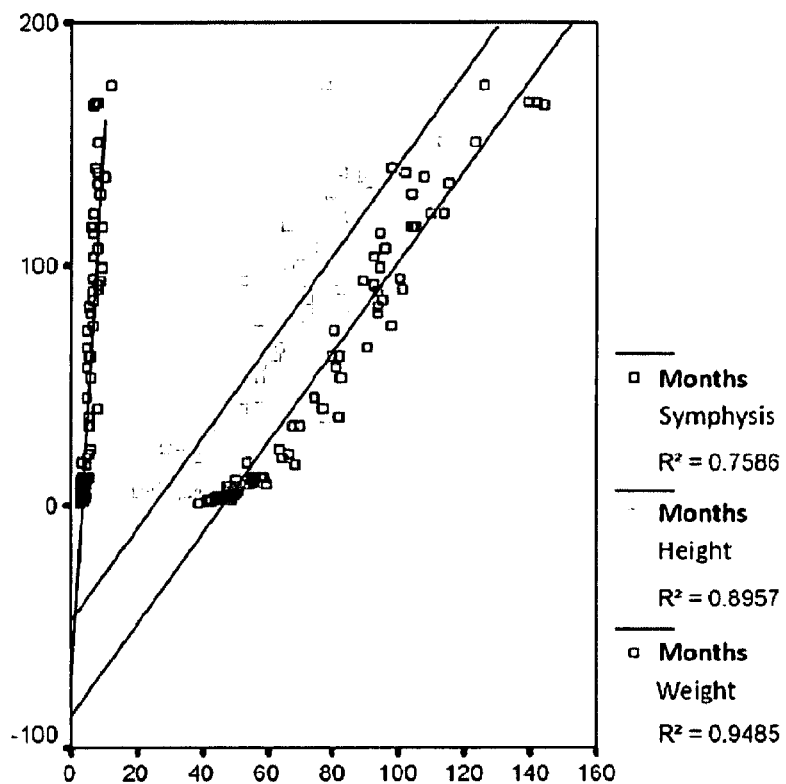
FIG. 14 shows a chart on the female pelvic cavity dimension growth and the distance between the anthropometric reference, which is the symphysis or pubic bone, and the lower part of the pelvic cavity at different ages, up to 200 months.

Besides the pelvic cavity height and width, there is a third anthropometric reference, which is the symphysis or pubic bone and, particularly, the distance between the symphysis and the pelvic cavity lower point. The above mentioned study analyzed the development of this distance at different ages and the relation between the symphysis and the pelvic cavity height and width (FIG. 14). Notwithstanding the above, other anthropometric reference points could be considered, such as iliac crests, among other.

In one of the invention embodiments, anthropometric connecting point may be unique in the device or at least two of them may be indicated, according to the maturity and gender the device is intended for.

In an additional embodiment, this invention includes a device that incorporates a frequency indicator and/or recorder to control the device useful life, so that the number of applications, exposures, and/or different treatments may be recognized and identified including, but not limited to, events such as washing, sterilization, or exposure to radiation. This is aimed at maintaining the device's effective radiological protection at high standards, as well as those of additional components incorporated to the device. If desired, this indicator and/or registry may be permanently attached to the device or it may be removed. At the same time, this indicator and/or registry may be seen by the user or operator, or it may be hidden in the device structure without affecting its capacity to record events to which the device is exposed to. In addition, it is possible to immediately verify this indicator and/or registry, or measurement systems may be required to verify event records in the device. Also, the invention seeks that the user may handle and use a device in optimal conditions, with no previous use or handling. An example of this indicator that is commercially available in the market is the chemical indicator in the form of a self-adhesive, "Gamma Radiation Indicator Label", from NAMSA, product codes CPI-R01, CPI-R02, and CPI-R03. These, when exposed to radiation, change color showing their exposure to radiation, and consequently the use of the protection device.

In a favorite indicator and/or registry embodiment, this may be selected from recording mechanisms, without being restricted to pH measuring systems, radiation recording systems, specific detectors for chemical components, temperature detectors, or any mechanism that allows a follow-up of the radiation protection device use and handling stages.

A complementary embodiment to this invention includes the incorporation of discreet functional areas containing an adherence additive to the radiological protection device which, in a complementary and synergic way to the anthropometric connecting point, allows keeping the device firmly adhered to the skin or to the corresponding substratum, in its correct application location, in order to provide an effective radiological protection to the area to be exposed. Adherence is aimed at preventing the shield from displacing, as it may leave areas of the body unprotected, or it may cover parts of the patient's bone structure, compromising the radiographic image quality and, therefore, diagnosis. The final result is to optimize diagnosis, preventing examination repetition and, finally, reduce the amount of radiation on the patient.

Another additional embodiment is a functional area that allows holding the device while it is applied to the patient. As an example, this area corresponds to the device upper part, where there is an holding flange above the functional area containing the radio-opaque material. The purpose is to fasten or hold the device during the examination, without using adhesive or complementing the latter, so that the device will not move and it will provide the correct protection.

In one of the favorite adhesive embodiments, this may be located in some or every discreet functional area of the device, with the possibility to select the area to be adhered to the individual, depending on the examination requirements. At the same time, the adhesive material may be changed of location, according to each particular case's requirements.

The above mentioned adhesive may be any adhesive material or system keeping the device fastened to the user's body during the corresponding examination, in vertical or horizontal position, standing or in movement. In addition, it is possible to regulate and/or keep its adhesive capacity even after repeated use, or not to keep it after its first use. Among the preferred adhesive products, we may mention, with no intention of being restricted to adhesives of water dispersion such as ethylene vinyl acetate/acrylic in proportions of 20%-80% solid, or in zinc oxide base, without restricting other adhesive solutions with or without hypo-allergenic characteristics in the market.

In other embodiment, the invention is related to a procedure and instructions for a correct placement of radiological protection devices. The process includes identification of anthropometric coordinates in the device user's anatomy and its alignment with the marks in the radiological protection device discreet functional areas, its surface rapprochement to fasten the device using adhesive, this way guaranteeing a correct adhesion and an effective protection of the areas to be exposed to radiation. At the same time, the invention includes the use of means to protect body areas from radiation or to attenuate or eliminate incidental radiation. In the case of the protection area, these may be used to manufacture the invention devices.

Example 1

In an invention embodiment, a used device is as indicated in FIG. 15a, and includes the following components (1) fastening flange, (2) upper coverage, (7) area containing the radiological protection radio-opaque material, (3) it is a discreet functional area that includes a radiation and use indicator, (4) it is a discreet functional area that includes an anthropometric reference point, and (6) corresponds to an area with contact adhesive.

Example 2

Figure 16A:
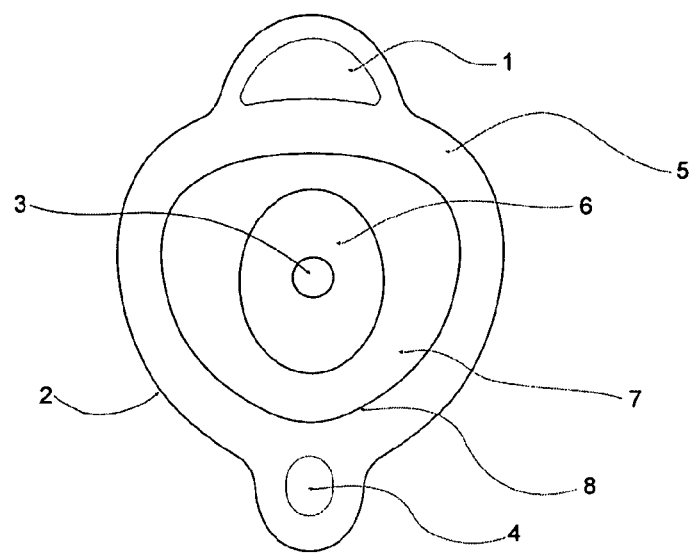
FIG. 16a shows a device, according to the invention, in a model proposed for females. Here, (1) represents a fastening flange, (2) is an upper covering, (3) corresponds to a radiation indicator and its use, (4) corresponds to an anthropometric connecting point. (5) corresponds to a back covering, (6) corresponds to a contact adhesive area, (7) shows the location of the radio-opaque material, and (8) corresponds to a radio-opaque material container.
Figure 16B:
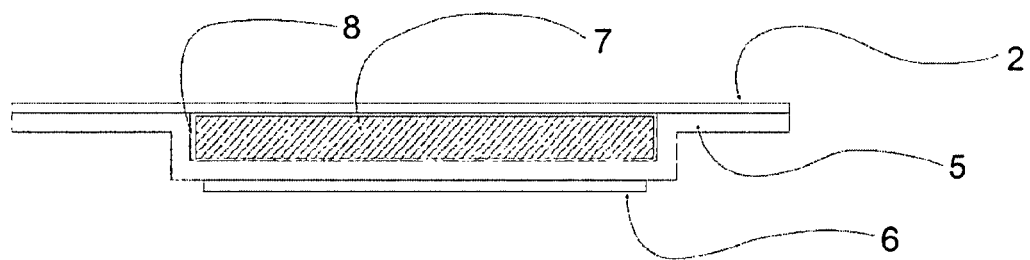
FIG. 16b shows a longitudinal cross-section of a device, according to the invention, in a model proposed for females. Here, (2) is an upper covering, (5) corresponds to a back covering, (6) corresponds to a contact adhesive area, (7) shows the location of the radio-opaque material, and (8) corresponds to a radio-opaque material container.
Figure 17:
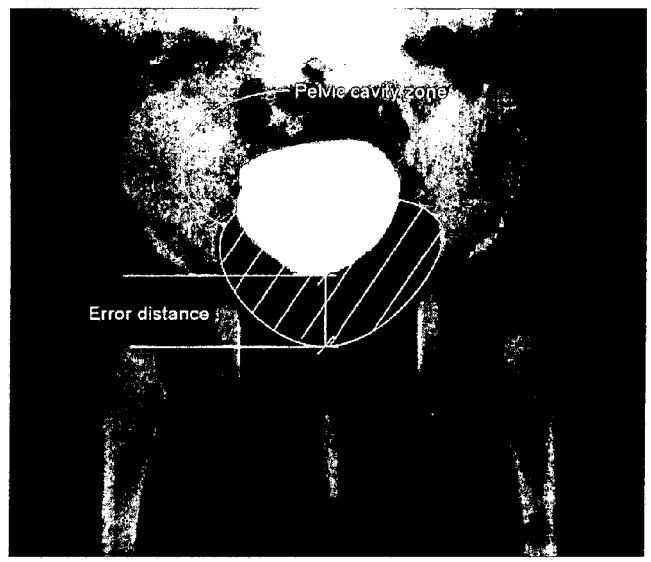
FIG. 17 corresponds to the radiography of a 2-month old girl with a hand-cut lead gonad shield (18) placed by the operator (technologist) with no anthropometric reference. Here, (10) is the pelvic cavity, and (11) is the protection error distance. It is clearly observed that in this case the radiological protection is dangerously displaced and does not cover the pelvic cavity.
Figure 18A:
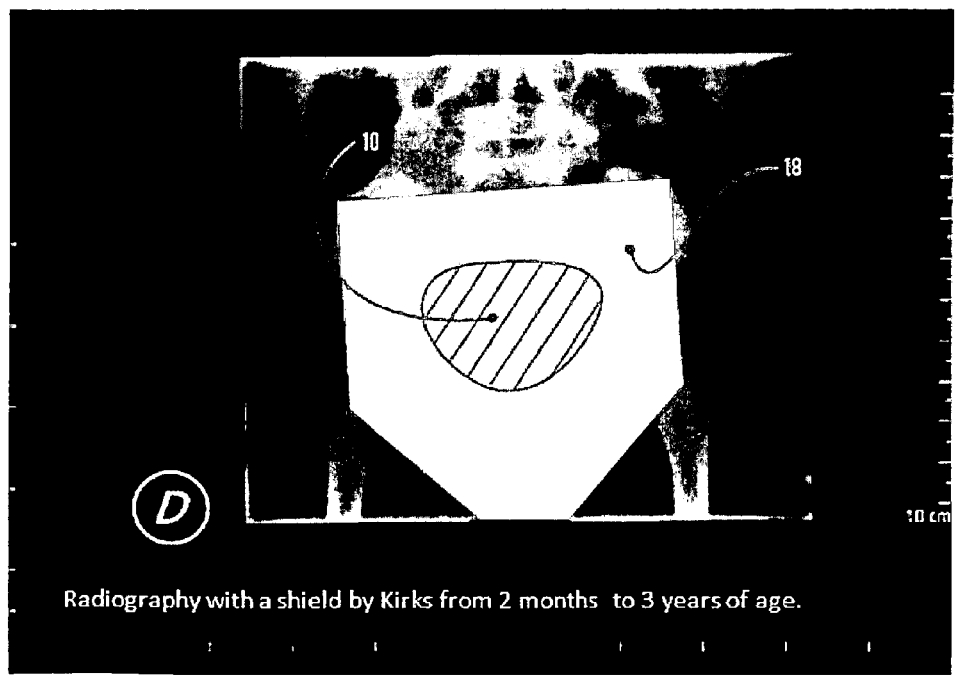
FIG. 18a corresponds to radiography with a KIRKS shield for 2 month to 3 year olds. Here, (10) is the pelvic cavity and (18) is KIRKS radio-opaque shield.
Figure 18B:
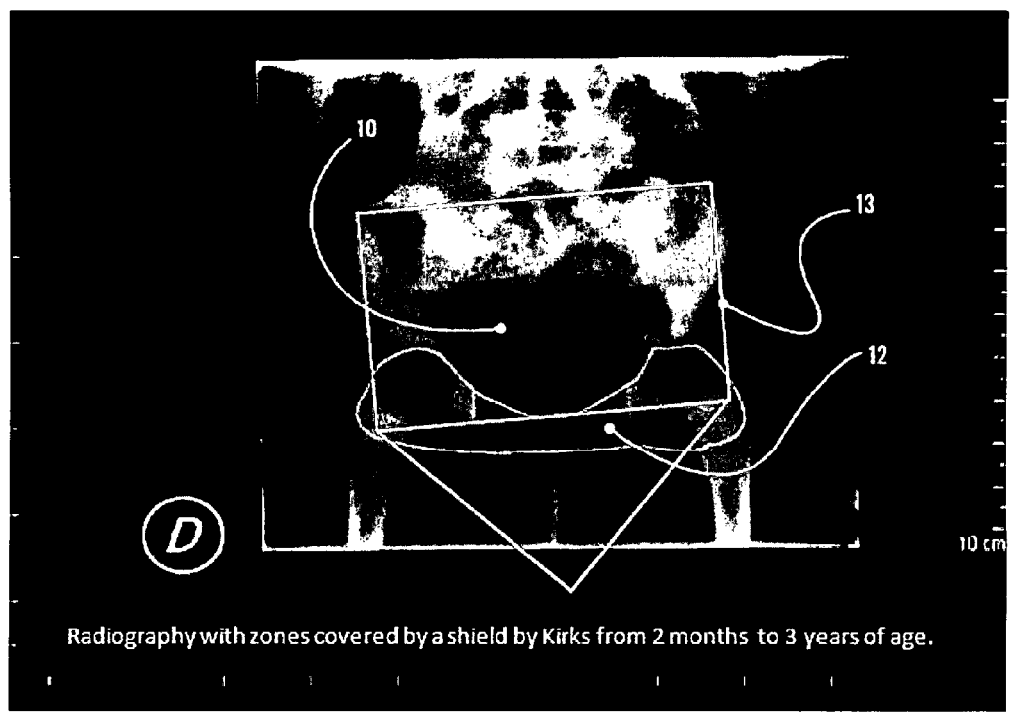
FIG. 18b corresponds to the radiography in 18b, with a KIRKS shield for 2 month to 3 year olds. Here, (10) is the pelvic cavity, (12) is the area of interest for medical diagnosis being obstructed by the radio-opaque shield, and (13) is the shield's edge or limit.
Figure 19A:
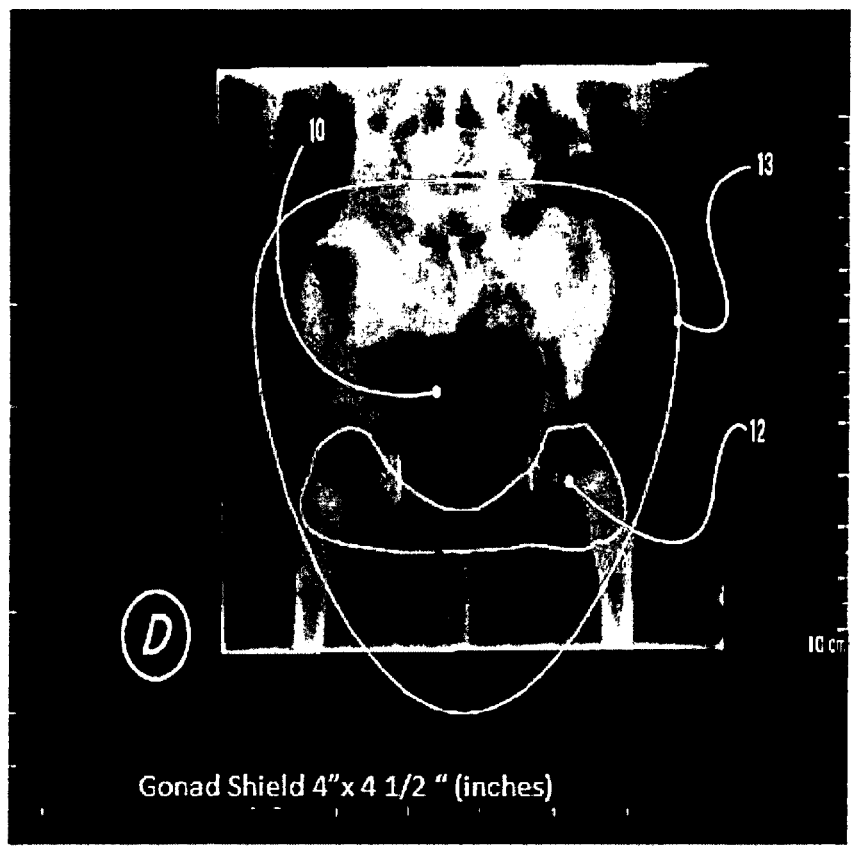
FIG. 19 corresponds to radiography with the PNWX Gonad Shield (4"×4½") from Oprax Medical International, small size, where (10) is the pelvic cavity, and (12) is the area of interest for medical diagnosis being obstructed by the radio-opaque shield, and (13) is the shield's edge or limit.
Figure 19B:
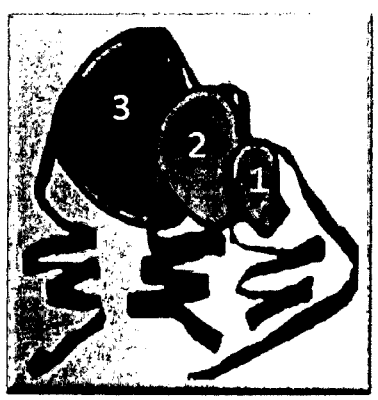
Figure 20A:
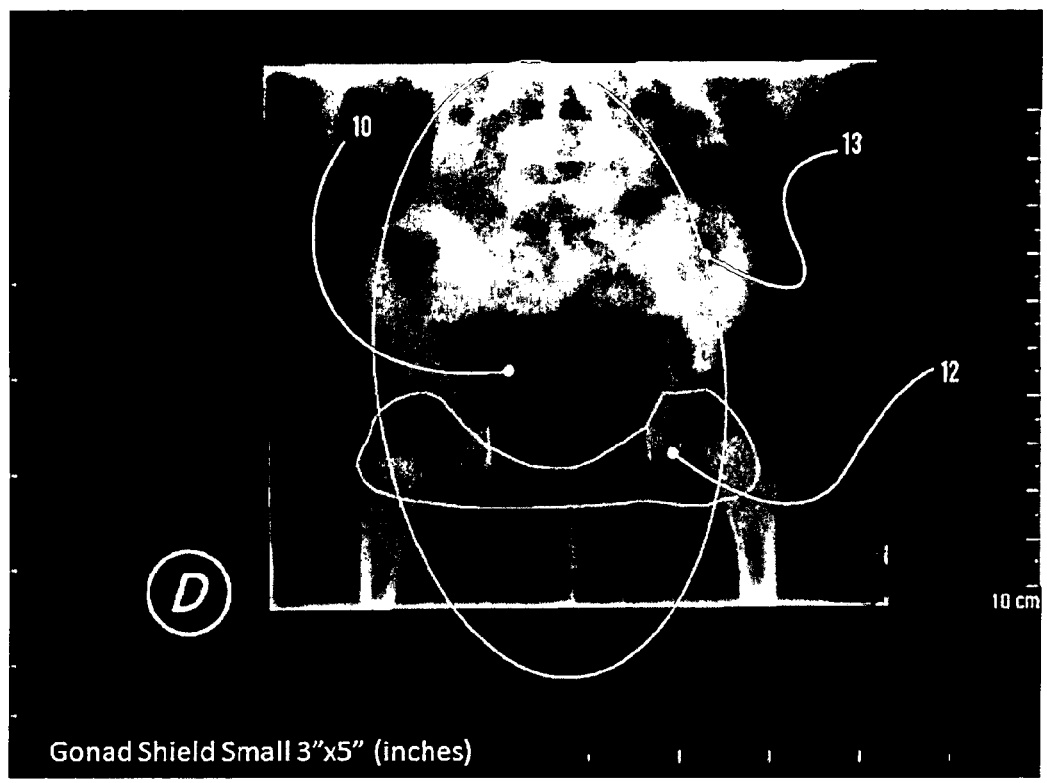
FIG. 20 corresponds to a radiography with the Techno-Aide Gonad Shield from Oprax Medical International, small size (3"×5"), where (10) is the pelvic cavity, and (12) is the area of interest for medical diagnosis being obstructed by the radio-opaque shield, and (13) is the shield's edge or limit.
Figure 20B:
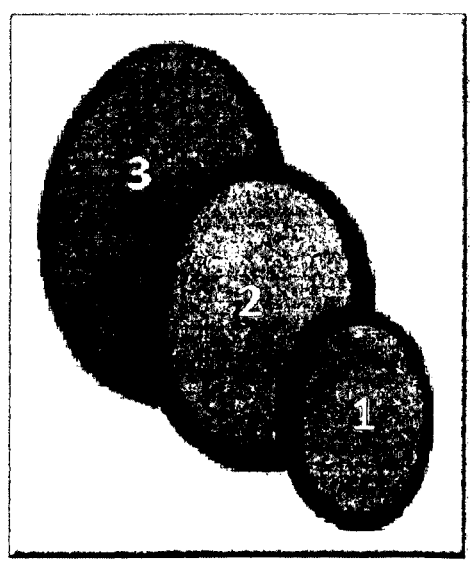

A favorite invention device is that represented in FIGS. 16a and 16b, proposed preferably for women. This device includes: (1) one fastening flange, (2) upper coverage, (4) an anthropometric connecting point to place on the pubic symphysis, (5) back coverage, (6) contact adhesive area, (7) the radio-opaque material location area, and (8) a radio-opaque material container.

Example 3

During a radiological examination, a device from this invention was used as those described in the previous examples. It is possible to notice that the radio-opaque area fully matches the area to be protected, without covering or interfering with other anatomic areas to be exposed for a correct examination and diagnosis (FIGS. 21a and 21b). Compared to radiological examinations carried out with other protection devices (examples 17 to 20), it is noticed that this invention is more effective and efficient.

Example 4

A female pediatric patient with 3 months of age required to undergo a hip x-ray examination to determine the development of the union of the hip socket and femoral head in order to know whether the patient has or will have in the future a bone disease called "hip dysplasia". For this procedure it is necessary to irradiate the hip area including radiation-sensitive organs such as the ovaries in order to diagnose correctly. In order to accurately place the radiological protection shield on an invisible gland, and in particular locating the radiation attenuation material, as in the case of the ovaries in the pelvic cavity, it is necessary to refer to points of the human body that are both recognizable detectable or identifiable.

This example uses the area of the pubic symphysis taking as an anthropometric reference to the highest bulge of the pubic symphysis, palpable from outside of the body. After having identified the location of this "anthropometric reference point" it is necessary to match this point with the "Anthropometric connecting point" present in the device, the distance of the connector element with the radiation attenuation material has the same distance or proportion to the "anthropometric reference point" and the area of interest to protect, in this case, the pelvic cavity. That is why when joining or fixing the protector to the patient by adhesive, velcro or snap-ons, to the reference point of the human body using the "Anthropometric connecting point" on the device, we locate the "Radiation attenuation material" over the area of interest protection, giving the patient a safe and accurate protection, which helps to protect sensitive areas of the human body at the same time achieving a useful image for medical diagnosis by not covering the areas of diagnostic interest.

Because the patient may move during the radiological examination and thus move the radiological protection or shield, you can visually obstruct areas of interest for medical diagnosis, so it is imperative to use a locking or fixation system that minimizes the risk of moving the radiation shield. A preferred solution to this problem is using adhesives that can bond and fix the protector directly to the patient's body or clothing, without excluding other alternatives that may offer similar or better results.

Other examples of reference points of the human body anthropometric that can be useful for protecting other body areas can be: the circumference of the penis base, testicles, nipples, lacrimal, nasal septum, thyroid, Adam's apple, the thyroid cartilage, the fold of the axilla, mammary gland end of the so-called "tail of Spence" among others.

1) The "radiation attenuation material" A may consider a larger size, less than or equal to the area to protect B.

2) The "radiation attenuation material" A may or may not have similarities in their form or shape the area to protect B.

3) The distance C is a distance that guides the location of A to be fixed on B by using D on E. E is a point of reference that is part of the human body and is to be used to guide the location by reference to their relationship to the area to be protected.

4) The distance C on the Device can be measured and defined from anywhere on the D area to anywhere in the A area, as for example between tangent and tangent, center and center, tangent and center, among others. For example according to FIG. 10b where the distance C is shown like the distance between highest palpable section to the symphysis relative to pelvic cavity in the FIG. 10b that is represented by the title "symphysis di" (distance) and the FIG. 14 where it shows a chart on the female pelvic cavity dimension growth and the distance between the "Anthropometric reference point", which is the symphysis or pubic bone and the lower part of the cavity at different ages.

5) The distance C in the human body can be measured and defined from anywhere in the "Anthropometric reference point" E with anywhere in the "Area to be protected" B, such as between tangent and tangent, center and center, tangent and center, between other.

6) The "Anthropometric reference point" E may be for example the highest area of the protuberance called symphysis pubis, which can be easily palpable from outside the human body, cartilaginous joint, located anteriorly of the bladder and above external genitals in women this is located on the vulva, another example is the diameter of the base of the penis, testicles, the nipple, the tear, the Adam's apple, the thyroid cartilage, among others.

The invention claimed is:

1. A sheet material providing radiological protection to a preselected area of the body and allowing radiological exposure to a preselected area of the body, said sheet material comprising:
 (a) an outer face and a body contacting face;
 (b) a radiation protecting attenuation material of pre-defined area and shape; and,
 (c) said material to be aligned, positioned and adhered to the patient's body by establishing a dimensional link between an anthropometric reference point and anthropometric coordinates located within the area of the body preselected for radiation exposure.

2. A method of allowing radiological exposure to a preselected area of the body, while maintaining radiological protection to preselected areas of the body comprising the steps of (a) providing a sheet material device; and, (b) attaching said device to a preselected area of the body, wherein said sheet material is comprised of:
   (a) an outer face and a body contacting face;
   (b) a radiation protecting attenuation section of predefined area and shape; and
   (c) said material to be aligned, positioned and adhered to the patient's body by establishing a dimensional link between an anthropometric reference point and anthropometric coordinates located within the area of the body preselected for radiation exposure.

3. A sheet material according to claim 1 wherein said preselected area of the body and the anthropometric reference point are in the pelvic area.

4. A sheet material according to claim 1 wherein said preselected area of the body is the genital and gonad area.

5. A sheet material according to claim 1 wherein said preselected area of the body and the anthropometric reference point are the pubic symphysis.

6. A method of allowing radiological exposure to selected areas of the body according to claim 2 wherein said sheet material device is protecting a male gonad area and the size of the protected area is proportional to the testicle width and height.

7. The sheet material according to claim 4 wherein the preselected area of the body for exposure is the female gonad area and the size of the preselected protected area is proportional to height and width of the pelvic cavity.

8. The sheet material according to claim 6 wherein the size of the protected area is in the width to height proportion of 0.4 to 1.0.

9. The sheet material according to claim 8 wherein the size of the protected area is in the width to height proportion of 0.65 to 0.85.

* * * * *